United States Patent
Woehr et al.

(10) Patent No.: US 8,328,762 B2
(45) Date of Patent: *Dec. 11, 2012

(54) CATHETER INSERTION DEVICE

(75) Inventors: Kevin Woehr, Felsberg (DE); Kenneth C. Raines, Bethlehem, PA (US)

(73) Assignee: B. Braun Melsungen AG, Melsungen (DE)

( * ) Notice: Subject to any disclaimer, the term of this patent is extended or adjusted under 35 U.S.C. 154(b) by 104 days.

This patent is subject to a terminal disclaimer.

(21) Appl. No.: 12/790,630

(22) Filed: May 28, 2010

(65) Prior Publication Data

US 2010/0249707 A1   Sep. 30, 2010

Related U.S. Application Data

(63) Continuation of application No. 10/520,325, filed as application No. PCT/EP03/07073 on Jul. 2, 2003, now Pat. No. 7,736,339.

(30) Foreign Application Priority Data

Jul. 4, 2002 (DE) .............................. 202 10 394 U

(51) Int. Cl.
*A61M 25/06* (2006.01)
*B23P 17/04* (2006.01)
(52) U.S. Cl. ..................................... 604/164.08; 29/428
(58) Field of Classification Search .............. 604/164.08, 604/168.01, 165.01; 29/428, 592
See application file for complete search history.

(56) References Cited

U.S. PATENT DOCUMENTS 3,601,151 A   8/1971 Winnard
4,143,853 A * 3/1979 Abramson ................. 251/149.1
4,387,879 A   6/1983 Tauschinski
4,449,693 A   5/1984 Gereg
(Continued)

FOREIGN PATENT DOCUMENTS

AU    2003246358 B2    1/2004
(Continued)

OTHER PUBLICATIONS

Patent Abstracts of Japan; entitled "Indwelling Puncture Needle With Wing Having Branching Part", Application No. 11-021665, Publication No. 2000-217925; Published Aug. 8, 2000, Applicant Hanako Medical KK (3 pages).

(Continued)

*Primary Examiner* — Kevin C Sirmons
*Assistant Examiner* — Michael J Anderson
(74) *Attorney, Agent, or Firm* — Klein, O'Neill & Singh, LLP

(57) ABSTRACT

Embodiments of a catheter insertion device are discussed comprising: an approximately hollow cylindrical catheter sleeve, at whose distal end a catheter is attached; a needle sleeve with a hollow needle, which is attached thereto and which, when ready for use, extends through the catheter sleeve and the catheter, and; a needle protective element that is arranged inside the catheter sleeve while being able to move on the needle. Said needle protective element has an engaging section that engages with an engaging device, which is formed in the vicinity of the needle tip, when the hollow needle is withdrawn from the catheter sleeve. A check valve is placed inside the catheter sleeve between the catheter and the needle protective element. The hollow needle, when ready for use, extends through said check valve, and the check valve automatically closes once the needle is withdrawn.

47 Claims, 3 Drawing Sheets

U.S. PATENT DOCUMENTS

| | | | |
|---|---|---|---|
| 4,511,359 A | 4/1985 | Vaillancourt | |
| 4,512,766 A * | 4/1985 | Vailancourt | 604/167.03 |
| 4,578,063 A | 3/1986 | Inman et al. | |
| 4,673,399 A | 6/1987 | Pruett | |
| 4,765,588 A | 8/1988 | Atkinson | |
| 4,772,266 A | 9/1988 | Groshong | |
| 4,795,432 A | 1/1989 | Karczmer | |
| 4,813,938 A | 3/1989 | Raulerson | |
| 4,842,591 A | 6/1989 | Luther | |
| 4,846,809 A | 7/1989 | Sims | |
| 4,874,377 A | 10/1989 | Newgard et al. | |
| 4,883,461 A | 11/1989 | Sawyer | |
| 4,917,668 A * | 4/1990 | Haindl | 604/167.03 |
| 4,927,414 A | 5/1990 | Kulli | |
| 4,929,235 A | 5/1990 | Merry et al. | |
| 4,929,241 A | 5/1990 | Kulli | |
| 4,944,725 A | 7/1990 | McDonald | |
| 4,952,207 A | 8/1990 | Lemieux | |
| 4,964,854 A | 10/1990 | Luther | |
| 4,966,586 A | 10/1990 | Vaillancourt | |
| 4,978,344 A | 12/1990 | Dombrowski et al. | |
| 5,051,109 A | 9/1991 | Simon | |
| 5,053,014 A | 10/1991 | Van Heugten | |
| 5,053,017 A | 10/1991 | Chamuel | |
| 5,062,836 A | 11/1991 | Wendell | |
| 5,084,023 A | 1/1992 | Lemieux | |
| 5,108,374 A | 4/1992 | Lemieux | |
| 5,127,905 A | 7/1992 | Lemieux | |
| 5,135,504 A | 8/1992 | McLees | |
| 5,147,327 A | 9/1992 | Johnson | |
| 5,154,703 A | 10/1992 | Bonaldo | |
| 5,156,596 A | 10/1992 | Balbierz et al. | |
| 5,158,554 A | 10/1992 | Jepson et al. | |
| 5,180,370 A | 1/1993 | Gillespie | |
| 5,188,607 A | 2/1993 | Wu | |
| 5,195,980 A | 3/1993 | Catlin | |
| 5,215,528 A | 6/1993 | Purdy et al. | |
| 5,234,410 A | 8/1993 | Graham et al. | |
| 5,242,393 A | 9/1993 | Brimhall et al. | |
| RE34,416 E | 10/1993 | Lemieux | |
| 5,269,771 A | 12/1993 | Thomas et al. | |
| 5,300,033 A | 4/1994 | Miller | |
| 5,312,355 A | 5/1994 | Lee | |
| 5,322,517 A * | 6/1994 | Sircom et al. | 604/198 |
| 5,328,482 A | 7/1994 | Sircom et al. | |
| 5,334,158 A | 8/1994 | McLees | |
| 5,334,159 A | 8/1994 | Turkel | |
| 5,344,408 A | 9/1994 | Partika | |
| 5,352,205 A | 10/1994 | Dales et al. | |
| 5,380,305 A | 1/1995 | Ghouri | |
| 5,405,323 A | 4/1995 | Rogers et al. | |
| 5,409,461 A | 4/1995 | Steinman | |
| 5,419,766 A | 5/1995 | Chang et al. | |
| 5,454,790 A | 10/1995 | Dubrul | |
| 5,456,675 A | 10/1995 | Wolbring et al. | |
| 5,458,640 A | 10/1995 | Gerrone | |
| 5,458,658 A | 10/1995 | Sircom | |
| 5,558,651 A | 9/1996 | Crawford et al. | |
| 5,562,630 A | 10/1996 | Nichols | |
| 5,562,633 A | 10/1996 | Wozencroft | |
| 5,584,809 A | 12/1996 | Gaba | |
| 5,601,536 A | 2/1997 | Crawford et al. | |
| 5,613,663 A | 3/1997 | Schmidt et al. | |
| 5,634,913 A * | 6/1997 | Stinger | 604/272 |
| 5,651,772 A | 7/1997 | Arnett | |
| 5,662,610 A | 9/1997 | Sircom | |
| 5,688,253 A | 11/1997 | Paradis | |
| 5,718,688 A | 2/1998 | Wozencroft | |
| 5,725,503 A | 3/1998 | Arnett | |
| 5,738,144 A | 4/1998 | Rogers | |
| 5,749,857 A | 5/1998 | Cuppy | |
| 5,779,681 A | 7/1998 | Bonn | |
| D397,434 S | 8/1998 | Pike | |
| 5,817,069 A | 10/1998 | Arnett | |
| 5,830,189 A | 11/1998 | Chang | |
| 5,851,196 A | 12/1998 | Arnett | |
| 5,865,806 A | 2/1999 | Howell | |
| 5,879,337 A | 3/1999 | Kuracina et al. | |
| 5,911,705 A | 6/1999 | Howell | |
| 5,911,710 A | 6/1999 | Barry et al. | |
| 5,935,104 A | 8/1999 | Janek et al. | |
| 5,954,698 A | 9/1999 | Pike | |
| 5,967,490 A | 10/1999 | Pike | |
| 5,971,957 A | 10/1999 | Luther et al. | |
| 6,001,080 A | 12/1999 | Kuracina et al. | |
| 6,004,294 A | 12/1999 | Brimhall et al. | |
| 6,077,244 A | 6/2000 | Botich et al. | |
| 6,080,137 A | 6/2000 | Pike | |
| 6,117,108 A * | 9/2000 | Woehr et al. | 604/110 |
| 6,171,287 B1 | 1/2001 | Lynn et al. | |
| 6,203,527 B1 * | 3/2001 | Zadini et al. | 604/110 |
| 6,228,060 B1 | 5/2001 | Howell | |
| 6,287,278 B1 * | 9/2001 | Woehr et al. | 604/110 |
| 6,352,520 B1 | 3/2002 | Miyazaki | |
| 6,379,333 B1 | 4/2002 | Brimhall et al. | |
| 6,379,372 B1 | 4/2002 | Dehdashtian et al. | |
| 6,443,927 B1 | 9/2002 | Cook | |
| 6,443,929 B1 | 9/2002 | Kuracina et al. | |
| 6,485,468 B2 | 11/2002 | Vojtasek | |
| 6,506,181 B2 | 1/2003 | Meng et al. | |
| 6,533,759 B1 | 3/2003 | Watson et al. | |
| 6,585,704 B2 * | 7/2003 | Luther et al. | 604/263 |
| 6,595,954 B1 | 7/2003 | Luther et al. | |
| 6,595,955 B2 | 7/2003 | Ferguson et al. | |
| 6,616,630 B1 * | 9/2003 | Woehr et al. | 604/110 |
| 6,629,959 B2 | 10/2003 | Kuracina et al. | |
| 6,652,486 B2 * | 11/2003 | Bialecki et al. | 604/110 |
| 6,652,490 B2 | 11/2003 | Howell | |
| 6,692,471 B2 | 2/2004 | Boudreaux | |
| 6,699,221 B2 | 3/2004 | Vaillancourt | |
| 6,709,419 B2 | 3/2004 | Woehr | |
| 6,749,588 B1 | 6/2004 | Howell et al. | |
| 6,916,311 B2 | 7/2005 | Vojtasek | |
| 7,125,396 B2 | 10/2006 | Leinsing et al. | |
| 7,736,339 B2 * | 6/2010 | Woehr et al. | 604/164.08 |
| 2002/0128604 A1 | 9/2002 | Nakajima | |
| 2004/0044313 A1 | 3/2004 | Nakajima | |
| 2004/0225260 A1 * | 11/2004 | Villa et al. | 604/164.01 |

FOREIGN PATENT DOCUMENTS

| | | |
|---|---|---|
| DE | 30 00 903 A1 | 1/1980 |
| DE | 31 00 622 A1 | 4/1980 |
| DE | 32 10 148 A1 | 9/1983 |
| DE | 44 34 569 A1 | 3/1995 |
| DE | 201 04 539 U1 | 1/2002 |
| EP | 0 414 997 A1 | 4/1990 |
| EP | 0 554 841 A1 | 8/1993 |
| EP | 0 747 084 A2 | 12/1996 |
| EP | 0 799 626 A1 | 10/1997 |
| EP | 1 101 508 A2 | 5/2001 |
| EP | 1 101 508 A3 | 8/2001 |
| EP | 1 180 381 A1 | 2/2002 |
| EP | 1 240 916 B1 | 9/2002 |
| EP | 1 374 942 A1 | 1/2004 |
| EP | 1 374 942 B1 | 1/2004 |
| GB | 2 118 440 A | 11/1983 |
| WO | WO 97/45151 | 12/1997 |
| WO | WO 98/53875 | 12/1998 |
| WO | WO 99/26682 | 6/1999 |
| WO | WO 2004/004819 A1 | 1/2004 |

OTHER PUBLICATIONS

Patent Abstracts of Japan; entitled "Safe Indwelling Needle", Application No. 2000-078335, Publication No. 2001-259029, Published Sep. 25, 2001, Applicant Medikit KK (7 pages).

Patent Abstracts of Japan; entitled "Safety Indwelling Needle", Application No. 2000-182911, Publication No. 2002-000727, Published Jan. 8, 2002, Applicant Medikit KK (4 pages).

Patent Abstracts of Japan; entitled "Indwelling Needle Structure", Applicant No. 2001-363865, Publication No. 2003-175112, Published Jun. 24, 2003, Applicant Mitsubishi Pencil Co LTD (5 pages).

Patent Abstracts of Japan; entitled "Indwelling Needle Structure and Seal Material Used Therefore", Application No. 2005-035112, Publication No. 2005-261938 A, Published Sep. 29, 2005, Applicant JMS Co LTD (5 pages).

Patent Abstracts of Japan; entitled "Indwelling Needle", Application No. 2004-143931, Publication No. 2005-323762, Published Nov. 24, 2005, Applicant Medikit KK (4 pages).

Patent Abstracts of Japan; entitled "Indwelling Needle", Application No. 1996-0040652, Publication No. 9206375, Published Aug. 12, 1997, Applicant: Togo Medikit KK (2 pages).

Brochure circulated in Japan, *JASDAQ*, 2 pgs, found at <http://www.medikit.co.jp>.

"Conical Fittings With 6% (Luer) Taper for Syringes, Needles and Certain Other Medical Euipment—Part 2: Lock fittings," International Standar, ISO 594-2, second edition, 1998, pp. 1-11, Technical Committee ISO/TC 84, Switzerland.

Office Action mailed May 29, 2007 from corresponding U.S. Appl. No. 10/520,325, filed Sep. 12, 2005.

Final Office Action mailed Nov. 14, 2007 from corresponding U.S. Appl. No. 10/520,325, filed Sep. 12, 2005.

Office Action mailed Sep. 26, 2008 from corresponding U.S. Appl. No. 10/520,325, filed Sep. 12, 2005.

Final Office Action mailed Mar. 30, 2009 from corresponding U.S. Appl. No. 10/520,325, filed Sep. 12, 2005.

Final Office Action mailed Jan. 19, 2010 from corresponding U.S. Appl. No. 10/520,325, filed Sep. 12, 2005.

Notice of Allowance mailed Feb. 25, 2010 from corresponding U.S. Appl. No. 10/520,325, filed Sep. 12, 2005.

Statutory Declaration of Kevin Woehr, Executed on Sep. 15, 2011, in the matter of Australian Patent Application No. 2003246358 and in the matter of Opposition thereto by Terumo Corporation, including Exhibits KW-1 to KW-7 (101 pages).

Statutory Declaration of William Samuel Hunter, Executed and Notarized on May 11, 2010, in the matter of Australian Patent Application No. 2003246358 and in the matter of Opposition thereto by Terumo Corporation (43 pages).

Statutory Declaration of Noel J. Akers, Executed and Notarized on Aug. 17, 2011, in the matter of Australian Patent Application No. 2003246358, including Exhibit NJA-1 (48 pages).

Annex 1: Facts and Arguments to the Notice of Opposition to a European Patent; Opponent Smith Medical ASD Inc.; Patentee B. Braun Melsungen AG for Opposed Patent No. EP 1 545 681 B1; dated Oct. 21, 2008 (133 pages).

Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Jan. 27, 2011 (77 pages).

Response to Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Oct. 21, 2011 (86 pages).

* cited by examiner

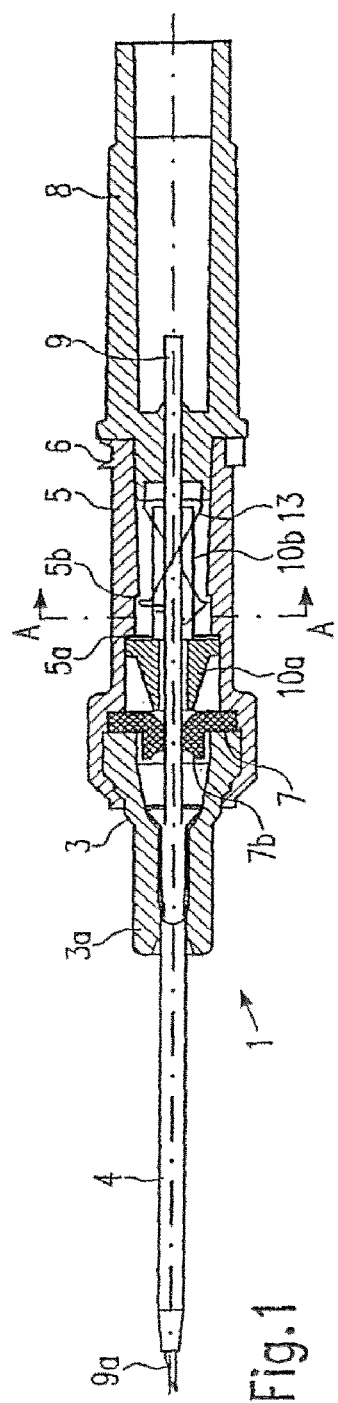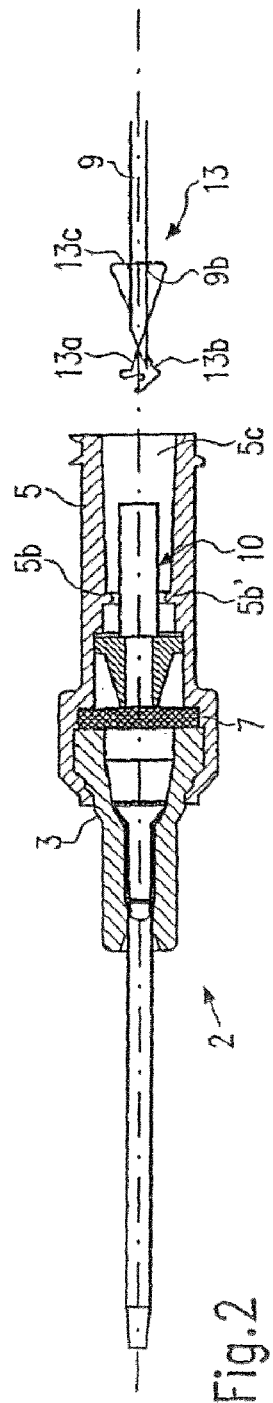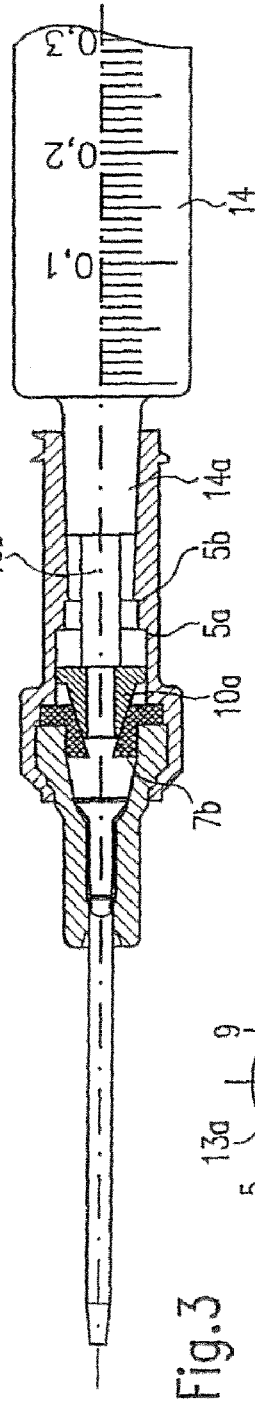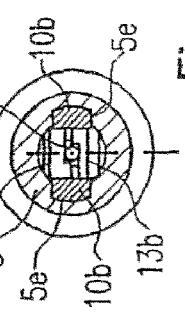
Fig. 1
Fig. 2
Fig. 3
Fig. 4

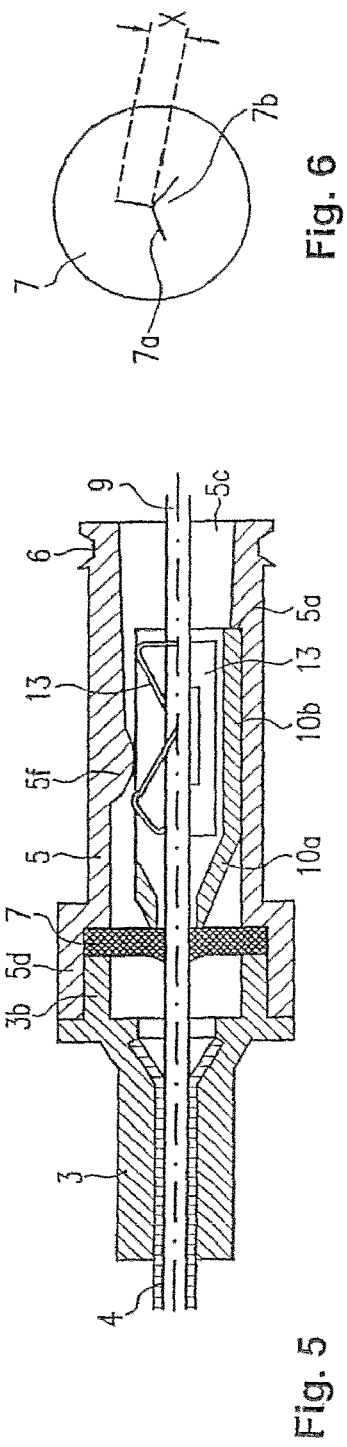
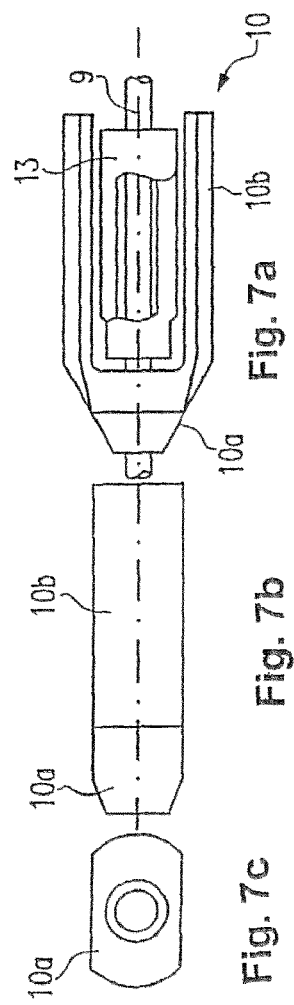

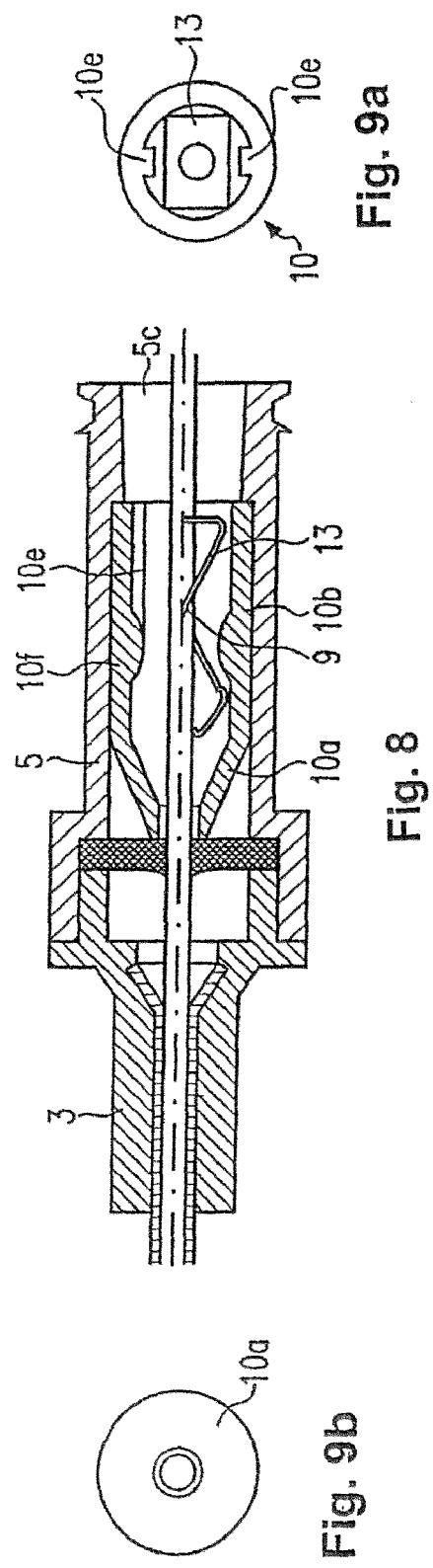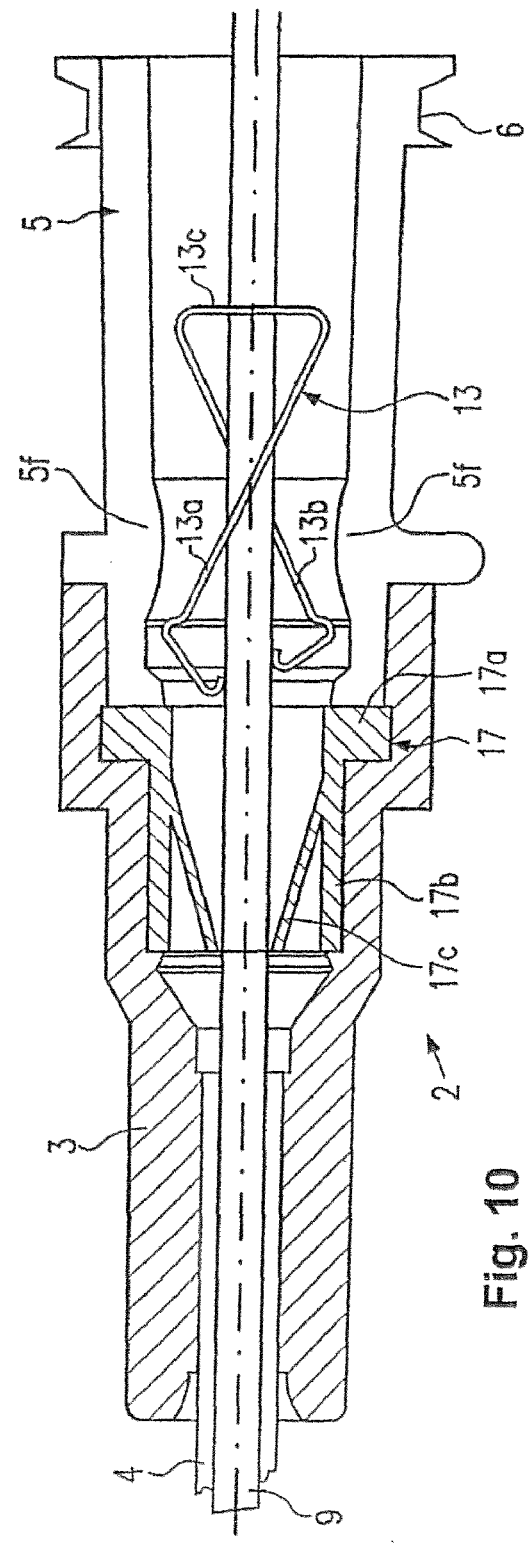

CATHETER INSERTION DEVICE

CROSS-REFERENCE TO RELATED APPLICATION

This is a continuation application of Ser. No. 10/520,325, filed Sep. 12, 2005 now U.S. Pat. No. 7,736,339, which is a national phase application of PCT No. PCT/EP03/07073 filed Jul. 2,2003; the contents of each of the foregoing are expressly incorporated herein by reference.

FIELD

Device, system, and method for a catheter insertion device are generally discussed herein with specific reference to catheter device having a valve opener and a valve.

BACKGROUND

A device of this kind is known from EP 352 928, wherein in a hollow catheter hub a needle guard element is arranged. On withdrawal of the hollow needle from the catheter over an engaging means near the tip of the hollow needle, the needle guard element engages with the engaging means and covers the tip when the hollow needle is separated from the catheter. In this design, after withdrawal of the hollow needle from the catheter, through this catheter blood can issue with which the operating personnel can come into contact.

The invention is based on the object of designing a catheter insertion device of the type described above such that an outflow of blood from the catheter is prevented after removal of the hollow needle with the needle guard element.

SUMMARY

This object is solved according to the invention by the features in the characterizing part of claim 1. In the ready position, a check valve is arranged in the catheter hub between the catheter and the needle guard element. Through this valve the hollow needle extends, so that after withdrawal of the hollow needle from the catheter the latter can be reliably closed such that an outflow of blood is prevented, while simultaneously the tip of the hollow needle is securely covered by the needle guard element so that the operating personnel cannot injure themselves on the needle tip.

BRIEF DESCRIPTION OF THE DRAWINGS

Exemplary embodiments of the invention are explained in more detail below with reference to the drawing, in which:

FIG. 1 shows a longitudinal section through a catheter insertion device in the ready position, FIG. 2 shows the catheter insertion device with the hollow needle removed, FIG. 3 shows the device with an attached syringe, FIG. 4 shows a sectional view along the line A-A in FIG. 1, FIG. 5 shows a longitudinal section through another embodiment, FIG. 6 shows a view of the valve disc, FIG. 7a-e shows different views of a valve actuating element, FIG. 8 shows a longitudinal section through a further embodiment, FIG. 9a,b shows front views of the valve actuating element of FIG. 8, and FIG. 10 shows a longitudinal section through a further embodiment.

DETAILED DESCRIPTION

FIG. 1 shows a catheter insertion device 1 having a catheter hub 2 which has a two-part form in the embodiment. A distal hub element 3 of the catheter hub has a holding section 3a in which a catheter 4 is press-fitted. The proximal end of the hub element 3 has an enlarged diameter with regard to the distal end and forms a connecting section with a hub element 5 whose distal end overlaps the proximal end of the hub element 3 and which is provided at its proximal end with a Luer thread 6. Between the two hub elements 3 and 5, a check valve in the form of a valve disc 7 is inserted and is fixed in place by the two hub elements 3 and 5.

In the ready position according to FIG. 1, there is inserted in the catheter hub 2 a needle hub 8 to which a hollow needle 9 is fixed which extends through the valve disc 7 and the catheter 4 so that the needle tip 9a is exposed. Between needle hub 8 and valve disc 7 there is displaceably arranged in the proximal hub element 5 a valve actuating element 10 which has a truncated cone-shaped locating section 10a which serves to open the valve disc 7, as FIG. 3 shows. On the proximal side, a plunger section 10b adjoins the locating section 10a and has a hollow space for receiving a needle guard element 13. In the embodiment shown, the plunger section 10b is formed by two spaced plungers between which the needle guard element in the form of a spring clip 13 is inserted, as shown in the cross-sectional view in FIG. 4.

On withdrawal of the hollow needle 9 from the catheter hub 2, an engaging means 9b (FIG. 2), provided near the needle tip 9a and having the form of a radial projection on the hollow needle which can be formed by light crimping, engages with the outer circumference of a bore in the rear wall 13c of the spring clip 13, so that the spring clip 13 is removed from the catheter hub with the needle 9, while simultaneously the spring arms 13a and 13b of the spring clip cover the needle tip, completely protecting and blocking it. In this separated position shown in FIG. 2, the valve disc 7, due to its elasticity, closes the through-hole for the hollow needle 9 so that no blood can flow out through the catheter 4. As FIG. 6 shows, the valve disc is provided for example with three slits 7a starting from the middle and extending radially over a short section X, forming elastic flaps 7b therebetween which can be expanded by the hollow needle.

FIG. 3 shows the insertion of a syringe 14 in the catheter hub 2, wherein the neck portion 14a of the syringe comes to abut on the plunger section 10b of the valve actuating element 10 and presses it against the valve disc 7, so that the truncated cone-shaped locating section 10a outwardly displaces the flaps 7b of the valve disc and thereby opens the valve, so that a liquid can be inserted from the syringe 14 into the catheter 4.

The incline of the truncated cone on the locating section 10a and the displacement path of the actuating element 10 relative to the valve disc 7 are designed such that due to the elasticity of the material of the valve disc 7, the flaps 7b displace the locating section 10a to the right in FIG. 3 when the syringe 14 is removed from the catheter hub 2. Hereby, the valve disc 7 is automatically closed, as the position in FIG. 2 shows.

In the hub element 5, there is formed by a shoulder 5a a stop for the actuating element 10, to define the position of the actuating element in the separated position in FIG. 2. Hereby, the truncated cone-shaped locating section 10a lies near the stop 5a, while its distal end abuts on the valve disc 7 as shown in FIG. 2. The radial slits 7a of the valve disc 7 are designed such that in the ready position in FIG. 1, the flaps 7b are bent radially upwards less than in the open position by the locating section 10a in FIG. 3.

As the cross-sectional view in FIG. 4 shows, the two plungers 10b of the valve actuating element 10 are guided in longitudinal grooves 5e of the hub element 5 and they project radially inwards into the bore 5c of the hub element 5, so that they form an abutting surface for the neck portion 14a of the syringe 14. The bore 5c in the hub element 5 is formed slightly conically corresponding to the conical neck portion 14a of a syringe.

On the inner circumference of the bore 5c of the hub element 5, a further shoulder 5b having a smaller diameter is formed, on which the radially outer areas of the spring arms 13a and 13b abut in the ready position in FIG. 1. Hereby, the spring clip 13 is fixed in its position in the hub element 5. When the needle huh 8 with the hollow needle 9 is removed from the catheter hub 2, first the spring clip 13 is held on the shoulder 5b by abutting until the radial projection 9b comes to abut on the rear wall 13c of the spring clip. In this position, the two spring arms 13a, 13b can be released from the shoulder 5b and spring back inwards to cover the needle tip, as FIG. 2 shows, whereupon the spring clip 13 with the hollow needle 9 can be removed from the catheter hub.

In the embodiment according to FIGS. 1 to 3, the distal end section of the hub element 5 is shrunk, welded or bonded onto the proximal end section of the hub element 3 after the valve actuating element 10 and the valve disc 7 are inserted in the hub element 5. It is also possible to join the two hub elements 3 and 5 to one another, for example by a thread which is secured against loosening after assembly. The spring clip 13 is inserted together with the hollow needle 9 in the bore 5c of the hub element 5 during assembly, wherein the radially outer areas of the spring arms 13a, 13b snap in at the shoulder 5b under elastic deformation.

Preferably, in front of the shoulder 5b a projection 5b' can be formed in the bore 5c of the hub element, as shown in FIG. 2. Hereby the snap-in and holding effect of the spring clip 13 is increased.

FIG. 5 shows a modified embodiment of the connection of the two hub elements 3 and 5, in which two cylindrical sections 3b and 5d engage in one another. A thread can be provided between these two cylindrical sections. However, it is also possible to bond or weld these two sections.

In this embodiment, the valve actuating element 10 is also modified in relation to the embodiment of FIGS. 1 to 3. FIG. 7a shows a side view of the approximately U-shaped actuating element 10 with the spring clip 13 inserted therein. As the side view rotated by 90.degree. in FIG. 7b shows, the locating section 10a is partly flattened on opposite sides so that the width of the plunger sections 10b extends into the locating section 10a. FIG. 7c is a front view from the left in FIG. 7b and shows the flattened structure of the locating section 10a. FIG. 7d is a sectional view along the central line in FIG. 7b. FIG. 7e shows a section through the valve actuating element 10 along the line B-B in FIG. 7d.

FIG. 5 shows the lower half of the valve actuating element 10 corresponding to the view in FIG. 7a, and the upper half in a sectional view rotated by 90.degree. corresponding to FIG. 7b. The shoulder 5a for positioning the valve actuating element 10 in the hub element 5 is hereby formed on the ends of the diametrically opposite grooves 5e (FIG. 4), so that the proximal ends of the plunger sections 10b abut on the shoulders 5a. Corresponding to the shoulder 5b in FIGS. 1 to 3 in the embodiment in FIG. 5, there is formed on the hub element 5 a projection 5f which projects inwards at diametrically opposite positions on the bore 5c of the hub element 5 and fixes the spring clip 13 in the hub element 5 until the spring arms 13a, 13b spring inwards over the needle tip and the spring clip with the hollow needle 9 is removed from the catheter hub.

FIG. 8 shows a modified embodiment having a hollow cylindrical valve actuating element 10 on whose inner circumference a projection 10f is formed for positioning the spring clip 13 inside the valve actuating element 10. FIG. 9a shows a front view of the valve actuating element 10 from the right and FIG. 9b shows a front view from the left in FIG. 8, wherein for locating the neck portion 14a of a syringe 14, in this embodiment radially inwardly projecting ribs 10e are formed which protrude radially into the bore 5c of the hub element 5, as the upper half of the valve actuating element in FIG. 8 shows, in which the sectional view of the lower half of the valve actuating element 10 is shown rotated by 90.degree. in relation to the upper half.

FIG. 10 shows a modified embodiment wherein between the two hub elements 3 and 5 a check valve 17 is inserted, which has a hollow cylindrical section 17b starting from a flange section 17a and abutting on the inner circumference of the hub element 3. From the inner circumference near the flange section 17a there start two opposite flaps 17c, which abut on the outer circumference of the hollow needle 9 in the ready position in FIG. 10. When the needle 9 is removed from the catheter hub 2, the elastically deformed flaps 17c move inwards and close the valve. In this embodiment, an actuating element for opening the valve 17 is not necessary, because the pressure of the fluid from the syringe 14 displaces the flaps 17c radially outwards so that the liquid can flow out through the valve 17. In this embodiment of a check valve, a so-called duck-bill valve is concerned, whose construction is in itself known.

In FIG. 10, in order to allow the spring clip 13 to be held in the catheter hub during withdrawal of the hollow needle 9 from the catheter hub 2 until the radial projection 9b on the hollow needle engages with the rear wall 13c to cover the needle tip, in this embodiment there is formed on the inner circumference of the proximal hub element 5 a projection 5f which extends radially inwards and on which the radially outer areas of the spring arms 13a and 13b come to abut and hold the spring clip until the spring arms spring back radially inwards to cover the needle tip. The inner diameter of the projection 5f is designed only slightly smaller than the maximum radial dimension at the spring arms 13a and 13b, so that during assembly the spring clip 13 can be inserted by slight pressure into the position in the catheter hub as shown in FIG. 10.

In the embodiment of a catheter insertion device according to FIGS. 1 to 9, in the position of the valve actuating element 10 in FIG. 2 the valve disc 7 can be opened by low pressure produced by the syringe 4 for drawing off liquid from the catheter, wherein the elastic flaps 7b are bent upward by the low pressure. In the embodiment of FIG. 10, a drawing-off of liquid from the catheter is not possible, because the duck-bill valve does not open when there is low pressure on the proximal side.

It is convenient to fabricate the check valve in the form of a valve disc 7 or of the flap valve 17 from elastic silicon, while a correspondingly rigid plastic material is used for the hub elements 3 and 5 and for the valve actuating element 10.

What is claimed is:

1. A catheter insertion device comprising:
  a catheter tube attached to an end of a catheter hub, the catheter tube comprising a lumen and the catheter hub comprising an interior cavity;

a needle having a needle shaft defining a needle axis attached to an end of a needle hub, said needle projecting through the lumen of the catheter tube;

a valve for regulating fluid flow positioned inside the interior cavity of the catheter hub and in mechanical communication with a movable valve actuating element for opening the valve, and wherein the valve remains inside the interior cavity of the catheter hub when the needle is removed from the catheter tube and the catheter hub; and a needle protective element positioned on the needle shaft and inside the catheter hub adjacent the valve and distal of the needle hub in a ready position.

2. The catheter insertion device of claim 1, wherein needle protective element comprises two arms that cross one another when viewed from a perspective perpendicular to the needle shaft.

3. The catheter insertion device of claim 1, wherein the needle protective element comprises a proximal wall comprising an opening having the needle passing therethrough.

4. The catheter insertion device of claim 1, wherein the valve is a disc having at least one slit formed therein.

5. The catheter insertion device of claim 1, wherein the movable valve actuating element comprises two leg sections comprising a space therebetween for accommodating the needle protective element.

6. The catheter insertion device according to claim 1, wherein the movable valve actuating element comprises a cylindrical section.

7. The catheter insertion device of claim 6, wherein the valve actuating element comprises two proximally extending legs defining a hollow space therebetween for receiving the needle protective device.

8. The catheter insertion device according to claim 1, wherein the catheter hub is made from two separately formed hub sections that are attached to one another.

9. A catheter insertion device comprising:

a catheter hub comprising an interior cavity, an opening at a proximal end, and a catheter tube attached thereto and extending from a distal end:

a needle having a needle shaft defining a needle axis projecting distally of an end of a needle hub, said needle projecting through the catheter tube and comprising a needle tip:

a valve for regulating fluid flow positioned inside the interior cavity of the catheter hub for regulating fluid flow into the interior cavity; said valve remaining inside the interior cavity of the catheter hub when the needle is removed from the catheter tube and the catheter hub and said valve being in contact with a valve actuating element when in an open position for fluid flow; and a needle protective device for preventing unintended needle sticks, said needle protective device positioned in-line with the catheter hub and the needle hub and having at least a portion extending distally of the proximal end of the catheter hub.

10. The catheter insertion device of claim 9, further comprising an enlarged needle section configured to engage an opening on the needle protective device.

11. The catheter insertion device of claim 9, wherein the needle protective device comprises a proximal wall and two arms extending distally thereof.

12. The catheter insertion device of claim 11, wherein the two arms intersect one another.

13. The catheter insertion device of claim 9, wherein the valve actuating element comprises two leg sections comprising a space therebetween for accommodating the needle protective device.

14. The catheter insertion device of claim 9, wherein the needle protective device comprises a resilient portion made from a metal material for moving the needle protective device from a ready position to a protected position.

15. The catheter insertion device of claim 9, wherein the valve actuating element is formed as a hollow cylinder with a truncated cone-shaped distal end section.

16. The catheter insertion device of claim 15, wherein the valve actuating element comprises two proximally extending legs defining a hollow space therebetween for receiving the needle protective device.

17. The catheter insertion device according to claim 9, wherein the needle protective device is biased against the needle.

18. A method of manufacturing a catheter insertion device comprising:

forming a catheter hub comprising a body comprising an interior cavity with an opening at a proximal end and attaching a catheter tube thereto;

positioning a valve in sealing communication with the interior cavity of the catheter hub for regulating fluid flow through the interior cavity;

positioning a valve actuating element in mechanical communication with the valve for deflecting the valve to permit fluid flow through the interior cavity of the catheter hub;

positioning a needle protective device at least partially inside the interior cavity of the catheter hub such that the needle protective device is in-line with the catheter hub and the valve actuating element;

positioning a needle hub having a needle attached thereto proximally of the catheter hub so that the needle projects through the catheter hub and the catheter tube; and wherein the valve remains inside the interior cavity of the catheter hub when the needle is removed from the catheter tube and the catheter hub.

19. The method of claim 18, wherein the needle comprises a sharp needle tip and an enlarged needle section near the needle tip.

20. The method of claim 18, wherein the valve has a plurality of radially elastically expandable valve flaps.

21. The method of claim 18, wherein the needle protective device comprises a guard section for blocking the needle tip.

22. The method of claim 18, wherein the valve actuating element is formed as a hollow cylinder with a truncated cone-shaped distal end section.

23. The method of claim 18, wherein the valve actuating element comprises two proximally extending legs defining a hollow space therebetween for receiving the needle protective device.

24. The method of claim 18, wherein the needle protective device comprises two arms extending distally of a proximal wall.

25. The method of claim 18, wherein the needle protective device comprises a resilient portion made from a metallic material for moving the needle protective device from a ready position to a protected position.

26. A catheter insertion device comprising a catheter hub comprising an interior cavity, an opening at a proximal end, and a catheter tube attached thereto and extending from a distal end; a needle having a needle shaft defining a needle axis projecting distally of an end of a needle hub, said needle projecting through the catheter tube and comprising a needle tip; a valve for regulating fluid flow positioned inside the interior cavity of the catheter hub for regulating fluid flow into the interior cavity; said valve remaining inside the interior cavity of the catheter hub when the needle is removed from the catheter tube and the catheter hub; a needle protective device for preventing unintended needle sticks, said needle protective device positioned in-line with the catheter hub and the needle hub and having at least a portion extending distally of the proximal end of the catheter hub; and wherein the needle protective device comprises a resilient portion for moving the needle protective device from a ready position to a protected position.

27. The catheter insertion device of claim 26, wherein the needle protective device comprises a proximal wall and two arms extending distally thereof.

28. The catheter insertion device of claim 26, further comprising an enlarged needle section configured to engage an opening on the needle protective device.

29. The catheter insertion device of claim 26, further comprising a valve actuating element disposed at least partially inside the catheter hub for abutting against the valve for fluid flow through the catheter hub.

30. The catheter insertion device of claim 27, wherein the two arms intersect one another.

31. The catheter insertion device of claim 29, wherein the valve actuating element comprises two leg sections comprising a space therebetween for accommodating the needle protective device.

32. The catheter insertion device of claim 29, wherein the valve actuating element comprises a cylindrical section.

33. The catheter insertion device of claim 15, wherein he valve actuating element further comprises at least two legs extending proximally of the truncated cone-shaped distal end section; said at least two legs define a gap for fluid flow to flow therebetween and wherein said at least two legs are configured to transfer a distally directed force to the truncated cone-shaped distal end section to open the valve.

34. The catheter insertion device of claim 15, wherein the hollow cylinder with the truncated cone-shaped distal end section further comprises a projection that projects radially outwardly of the hollow cylinder and abuts a shoulder in the interior cavity of the catheter hub.

35. The catheter insertion device of claim 33, wherein the hollow cylinder with the truncated cone-shaped distal end section further comprises a projection that projects radially outwardly of the hollow cylinder and abuts a shoulder in the interior cavity of the catheter hub.

36. The catheter insertion device of claim 15, wherein the valve actuating element further comprises at least one gap at a proximal plunger section to form a non-continuous perimeter section along a radial direction.

37. The catheter insertion device of claim 36, wherein the at least one gap is at a most proximal end of the proximal plunger section.

38. The catheter insertion device of claim 22, wherein the valve actuating element further comprises at least two legs extending proximally of the truncated cone-shaped distal end section; said at least two legs define a gap for fluid flow to flow therebetween and wherein said at least two legs are configured to transfer a distally directed force to the truncated cone-shaped distal end section to open the valve.

39. The catheter insertion device of claim 32, wherein the valve actuating element further comprises at least two legs extending proximally of the cylindrical section: said at least two legs define a gap for fluid flow to flow therebetween and wherein said at least two legs are configured to transfer a distally directed force to the cylindrical section to open the valve.

40. The catheter insertion device of claim 32, wherein the cylindrical section comprises a tapered distal end section and a projection that projects radially outwardly of the cylindrical section and abuts a shoulder in the interior cavity of the catheter hub.

41. The catheter insertion device of claim 32, wherein the valve actuating element further comprises at least one gap at a proximal plunger section and the valve comprises at least one slit.

42. The catheter insertion device of claim 41, wherein the at least one gap is at a most proximal end of the proximal plunger section.

43. The catheter insertion device of claim 41, further comprising a luer tip positioned inside the opening at the proximal end of the catheter hub after the needle protective device is in the protected position.

44. The catheter insertion device of claim 43, wherein the luer tip abuts the proximal plunger section of the valve actuating element and the at least one gap is located therebetween.

45. The catheter insertion device of claim 32, further comprising a fluid path between a distal most end of the valve actuating element and a proximal most end of the valve actuating element for fluid communicating with at least one slit in the valve.

46. The catheter insertion device of claim 45, further comprising a projection that extends radially outwardly of the cylindrical section for engaging a shoulder in the catheter hub.

47. The catheter insertion device of claim 46, further comprising a gap at the proximal plunger section of the valve actuating element.

* * * * *

UNITED STATES PATENT AND TRADEMARK OFFICE
CERTIFICATE OF CORRECTION

PATENT NO. : 8,328,762 B2
APPLICATION NO. : 12/790630
DATED : December 11, 2012
INVENTOR(S) : Kevin Woehr et al.

Page 1 of 1

It is certified that error appears in the above-identified patent and that said Letters Patent is hereby corrected as shown below:

On Title page 3, Item [56] in column 1, line 10, under "Other Publications", Delete "Euipment" and insert -- Equipment --, therefor.

On Title page 3, Item [56] in column 1, line 11, under "Other Publications", Delete "Standar," and insert -- Standard, --, therefor.

In column 3, line 6, Delete "lob" and insert -- 10b --, therefor.

In column 3, line 18, Delete "huh" and insert -- hub --, therefor.

In column 5, line 39, In Claim 9, Delete "end:" and insert -- end; --, therefor.

In column 5, line 43, In Claim 9, Delete "tip:" and insert -- tip; --, therefor.

In column 7, line 28, In Claim 33, Delete "he" and insert -- the --, therefor.

In column 8, line 12, In Claim 39, Delete "section:" and insert -- section; --, therefor.

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,328,762 B2
APPLICATION NO. : 12/790630
DATED : December 11, 2012
INVENTOR(S) : Woehr et al.

Page 1 of 1

It is certified that error appears in the above-identified patent and that said Letters Patent is hereby corrected as shown below:

In the Claims

In column 8, line 4, claim 38, delete "The catheter insertion device of claim 22" and insert -- The method of claim 22 --, therefor.

Signed and Sealed this
Twentieth Day of January, 2015

Michelle K. Lee
*Deputy Director of the United States Patent and Trademark Office*